(12) United States Patent
Kirk et al.

(10) Patent No.: US 6,326,186 B1
(45) Date of Patent: Dec. 4, 2001

(54) METHOD FOR REDUCING AMINO ACID BIOSYNTHESIS INHIBITING EFFECTS OF A SULFONYL-UREA BASED COMPOUND

(75) Inventors: Ole Kirk, Virum; Anders Ohmann, Brønshøj, both of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/416,976

(22) Filed: Oct. 13, 1999

Related U.S. Application Data
(60) Provisional application No. 60/105,146, filed on Oct. 21, 1998.

(30) Foreign Application Priority Data

Oct. 15, 1998 (DK) .................................. PA 1998 01325

(51) Int. Cl.$^7$ ....................................... B09B 3/00
(52) U.S. Cl. ........................................ 435/262.5; 435/267
(58) Field of Search ............... 435/41, 128, 130, 435/166, 262, 262.5, 267

(56) References Cited

U.S. PATENT DOCUMENTS 5,429,949 * 7/1995 Radosevich et al. ............. 435/252.1
6,100,382 * 8/2000 Wolfe et al. ........................ 530/370

FOREIGN PATENT DOCUMENTS

WO 94/23857    10/1994  (WO).
WO 97/19176     5/1997  (WO).

* cited by examiner

*Primary Examiner*—David A. Redding
(74) *Attorney, Agent, or Firm*—Elias J. Lambiris; Jason I. Garbell

(57) ABSTRACT

A method has been found for reducing amino acid biosynthesis inhibiting effect of a sulfonyl-urea based compound of the general formula:

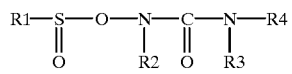

comprising contacting in an aqueous solution said sulfonyl-urea based compound with an enzyme capable of reducing said amino acid biosynthesis inhibiting effect.

14 Claims, No Drawings

METHOD FOR REDUCING AMINO ACID BIOSYNTHESIS INHIBITING EFFECTS OF A SULFONYL-UREA BASED COMPOUND

CROSS-REFERENCE TO RELATED APPLICATIONS

This application claims priority under 35 U.S.C. 119 of Danish application PA 1998 01325 filed Oct. 15, 1998 and of U.S. Provisional application No. 60/105,146 filed Oct. 21, 1998, the contents of which are fully incorporated herein by reference.

TECHNICAL FIELD

The present invention relates to a method for enzymatic treatment of sulfonyl-urea based compounds. More specifically the invention relates to a method, wherein an enzyme is employed to treat sulfonyl-urea based compounds, which are highly potent inhibitors of biosynthesis of amino acids in various organisms, and which may be used as powerful herbicides, pesticides or as drugs. Even more specifically the invention relates to a method for reducing the amino acid biosynthesis inhibiting effect of sulfonyl-urea based compounds to prevent unintended contamination of biological material sensitive to such compounds is by devices used at both sensitive and insensitive biological material.

BACKGROUND ART

Sulfony

Recovery and formulation of the enzyme.

The fermentation broth or enzyme solution or concentrates thereof may be further processed to obtain 1) a stable liquid composition by addition of conventional stabilizers, 2) a slurry composition or 3) a composition with the enzyme in a protected form. Protected enzymes may be prepared according to the method disclosed in EP-A-238,216.

Solid enzyme preparations or composition may be prepared from the broth or enzyme solution or concentrates thereof broth by precipitation with salts, such as $Na_2SO_4$ or water-miscible solvents, such as ethanol or acetone. Removal of the water in the broth by suitable drying methods, such as spray-drying, may also be employed. A preferred solid enzyme composition is a granulate, most preferred a dust free granulate. Dust free granulates may be produced, e.g. as disclosed in U.S. Pat. No. 4,106,991 and U.S. Pat. No. 4,661,452 and may optionally be coated by methods known to the art.

The Sulfonyl-urea Based Compound

The sulfonyl-urea based compounds are of the general formula:

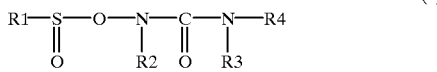
(1)

where R1 and R4 may be selected from the group of residues consisting of $C_{1-18}$-alkyl, monocyclic aromatic, dicyclic aromatic, polycyclic aromatic and heteroaromatic, while R2 and R3 substituent may be selected from the group consisting of hydrogen, methyl, ethyl and butyl. in a preferred embodiment R1 is a mono-aromatic group and R4 is a heteroaromatic group, e.g. R1 may be a phenyl group and R4 may be selected from the group consisting of pyridine, pyrazine, pyridazine, pyrimidine and triazine. Thus the a preferred sulfonyl-urea based compound may be of the formula:

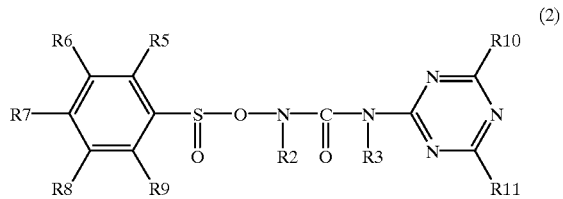
(2)

Said R1 and R4 substituents may further be substituted with substituents selected from the group consisting of halogen, sulfo, sulfonato, sulfamino, sulfanyl, amino, amido, nitro, azo, imino, carboxy, cyano, formyl, hydroxy, halocarbonyl, carbamoyl, carbamidoyl, phosphonato, phosphonyl, $C_{1-18}$-alkyl, $C_{1-18}$-alkenyl, $C_{1-18}$-alkynyl, $C_{1-18}$-alkoxy, $C_{1-18}$-oxycarbonyl, $C_{1-18}$-oxoalkyl, $C_{1-18}$-alkyl sulfanyl, $C_{1-18}$-alkyl sulfonyl and $C_{1-18}$-alkyl imino or amino which is substituted with one, two or three $C_{1-18}$-alkyl groups. Accordingly the sulfonyl-urea based compound may preferably be selected from the group consisting of

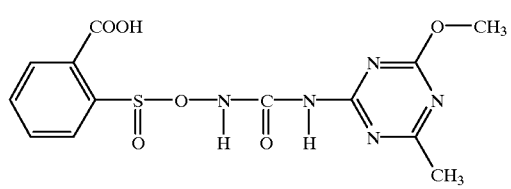
(3)

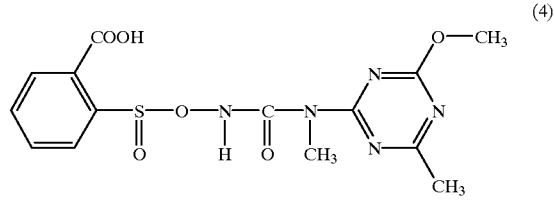
(4)

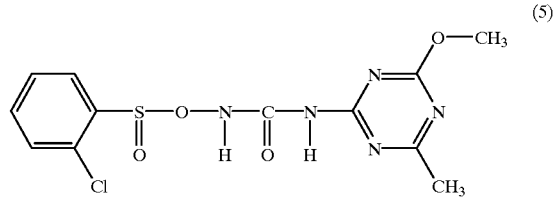
(5)

and

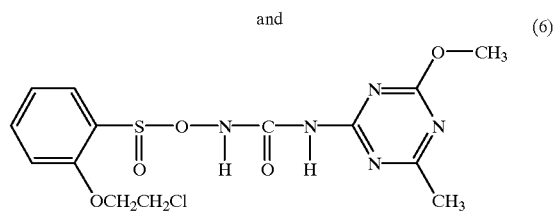
(6)

Further preferred sulfonyl-urea based compounds are biocides such as a herbicide, pesticide, fungicide or bactericide and preferably acts as amino acid biosynthesis inhibitors.

Applications

The method of the invention comprises as said contacting in an aqueous solution the sulfonyl-urea based compound with an enzyme capable of reducing the amino acid biosynthesis inhibiting effect of the sulfonyl-urea based compound. Typically the reduction of amino acid biosynthesis inhibiting effect may be obtained from contact with a hydrolase enzyme which will result from a hydrolytic degradation or digestion of the sulfonyl-urea based compound.

The method may suitably be used to clean devices used for handling the compounds, which devices are also used for purposes where the presence of sulfonyl-urea based compounds is highly undesirable. Such devices may e.g. be agricultural or horticultural crop spraying devices used both to spray plants, which is insensible to sulfonyl-urea based compounds and plants which is sensible to sulfonyl-urea based compounds. The method may also be used to avoid general environmental contamination by treating e.g. left overs of spraying solutions comprising sulfonyl-urea based compounds, and waste waters used to clean or flush the spraying device. Accordingly the invention provides a method for cleaning a spraying device or a waste water containing sulfonyl-urea based compounds by contacting the spraying devices or waste water with an enzyme.

Materials and Methods

All chemicals should be of analytical grade and may be obtained from Merck (Darmstadt, Germany). Chlorsulfuron (1-(2-chlorophenylsulfonyl)-3-(4-methoxy-6-methyl-1,3,5-triazin-2-yl)urea) is available from E.I. du Pont de Nemours & Co. (Inc.) under the trademarks Glean and Telar.

As a method of measuring the Glean and Telar and the degradation products upon treatment with enzyme, HPLC is performed using a LC-6A HPLC system (Shimadzu, Japan) with UV-detection (280 nm), employing a gradient of acetonitrile in water (20–80% over 25 min.) and a LiChrosorb RP-18 (10 μm) reversed phase column (250×4.6 mm I.D.).

A second assay for detecting levels of sulfonyl-urea based compounds in samples was developed in which 2.25 mg chorsulfuron was dissolved in a 1500 μl BR buffer pH 7, which has been added 125 μl acetone and 125 μl ethanol. The BR buffer was 40 mM phosphoric acid, 40 mM acetic acid, 40 mM boric acid adjusted with 0.2N NaOH. Samples of typically 20 μl of enzyme stock solution (dependent on the concentration) was added to this mixture and the resulting mixture was incubated at 37° C. for 24 hours in a thermo mixer after which break-down of chorsulfuron could be monitored by Thin Layer Chromatography (TLC) employing Si-60 plates eluted with a solvent of toluene, methylenechloride and ethanol in a ratio of 5:4:1 ($R_f$ values: chlorsulfuron 0.37, methylsyringate 0.51).

Urease obtained from Jack Beans (Type VI) obtained from Sigma (art. No. U 2125) is used to degrade the Chlorsulfuron (1-(2-chlorophenylsulfonyl)-3-(4-methoxy-6-methyl-1,3,5-triazin-2-yl)urea).

The invention is illustrated by the following examples, which in no way is intended to be limiting to the scope of the invention.

EXAMPLES

Example 1
Degradation of Chlorsulfuron Using Urease 1 mg Urease (corresponding to approx. 125 Urease units) is added to a solution of 100 mg chlorosulfuron in 500 ml phosphate buffer (0.1M, pH 7.0). The solution is stirred on a magnetic stirrer and samples are drawn at regular time intervals, e.g. 1–5 minutes for 30 minutes and analyzed by HPLC to monitor the sample content of chlorosulfuron. A control sample prepared without the addition of Urease chlorosulfuron is also analyzed by HPLC for comparison and relative measurement of the degree of the enzymatic degradation of the chlorosulfuron.

What is claimed is:

1. A method for reducing the amino acid biosynthesis inhibiting effect of a sulfonyl-urea based compound of the general formula:

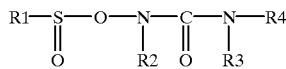

comprising contacting in an aqueous solution said sulfonyl-urea based compound with an isolated enzyme.

2. The method according to claim 1, further characterized in that the enzyme is a hydrolase (EC 3.-.-.-).

3. The method according to claim 2, wherein said hydrolase is selected from the group consisting of esterase (EC 3.1.-.-), peptidase (EC 3.4.-.-), hydrolase acting on carbon-nitrogen bonds other than peptide bonds (EC 3.5.-.-) and sulfohydrolase (EC 3.10.-.-).

4. The method according to claim 3, wherein said esterase is selected from the group consisting of carboxylic ester hydrolase (EC 3.1.1.-) and sulphatase (EC 3.1.6.-).

5. The method according to claim 4, wherein said carboxylic ester hydrolase is selected from the group consisting of carboxyl esterase (EC 3.1.1.1) and lipase (EC 3.1.1.3).

6. The method according to claim 3, wherein said hydrolase acting on carbon-nitrogen bonds other than peptide bond is selected from the group consisting of amidase (EC 3.5.1.4) and urease (EC 3.5.1.5).

7. The method according to claim 6, wherein said urease is obtained from Jack Beans.

8. The method according to claim 1, wherein R1 and R4 of said general formula for the sulfonyl-urea based compound is selected from the group of residues consisting of $C_{1-18}$-alkyl, monocyclic aromatic, dicyclic aromatic, polycyclic aromatic and heteroaromatic and R2 and R3 is selected from the group consisting of hydrogen, methyl, ethyl and butyl.

9. The method according to claim 8, wherein R1 is a mono-aromatic group and R4 is a heteroaromatic group.

10. The method according to claim 9, wherein said mono-aromatic group is a phenyl group and said heteroaromatic group is selected from the group consisting of pyridine, pyrazine, pyridazine, pyrimidine and triazine.

11. The method according to claim 10, wherein the sulfonyl-urea based compound is of the formula:

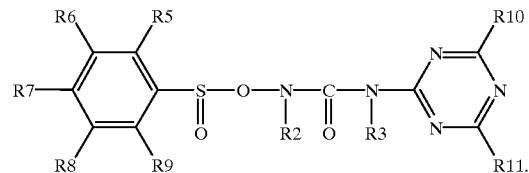

12. The method according to claim 8, wherein said R1 and R4 substituents further is substituted with substituents selected from the group consisting of halogen, sulfo, sulfonato, sulfamino, sulfanyl, amino, amido, nitro, azo, imino, carboxy, cyano, formyl, hydroxy, halocarbonyl, carbamoyl, carbamidoyl, phosphonato, phosphonyl, $C_{1-18}$-alkyl, $C_{1-18}$-alkenyl, $C_{1-18}$-alkynyl, $C_{1-18}$-alkoxy, $C_{1-18}$-oxycarbonyl, $C_{1-18}$-oxoalkyl, $C_{1-18}$-alkyl sulfanyl, $C_{1-18}$-alkyl sulfonyl and $C_{1-18}$-alkyl imino or amino which is substituted with one, two or three $C_{1-18}$-alkyl groups.

13. The method according to claim 8, wherein said sulfonyl-urea based compound is selected from the group of compound having the formulas of:

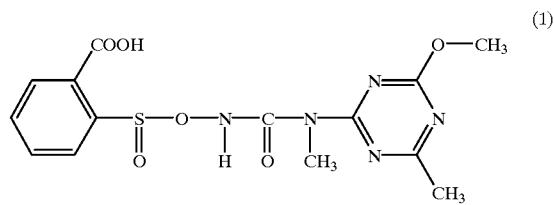

(1)

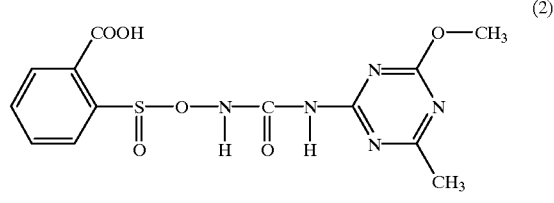

(2)

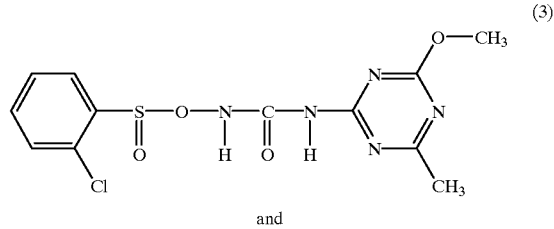

(3)

and

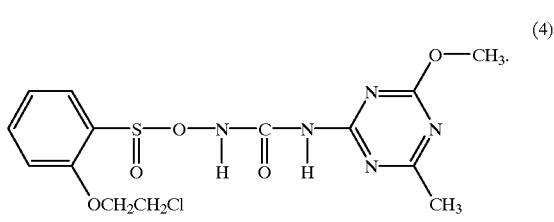

(4)

14. The method according to claim 1, wherein the sulfonyl-urea based compound is present in a spraying device or a waste water.

* * * * *